(12) United States Patent
Bussey et al.

(10) Patent No.: US 11,280,096 B1
(45) Date of Patent: Mar. 22, 2022

(54) CUSHIONING PREFORM FOR FLOORING

(71) Applicants: Harry Bussey, Singer Island, FL (US); Buddy Harry Bussey, III, Atlantic Highlands, NJ (US)

(72) Inventors: Harry Bussey, Singer Island, FL (US); Buddy Harry Bussey, III, Atlantic Highlands, NJ (US)

( * ) Notice: Subject to any disclaimer, the term of this patent is extended or adjusted under 35 U.S.C. 154(b) by 151 days.

(21) Appl. No.: 16/409,050

(22) Filed: May 10, 2019

Related U.S. Application Data (60) Provisional application No. 62/753,278, filed on Oct. 31, 2018.

(51) Int. Cl.
| | | |
|---|---|---|
| *E04F 15/22* | (2006.01) | |
| *B32B 27/06* | (2006.01) | |
| *B32B 27/32* | (2006.01) | |
| *E04F 15/18* | (2006.01) | |
| *E04F 15/20* | (2006.01) | |
| *E04F 15/02* | (2006.01) | |
| *E04F 15/10* | (2006.01) | |
| *E04B 9/04* | (2006.01) | |
| *E04B 1/84* | (2006.01) | |

(52) U.S. Cl.
CPC .......... *E04F 15/22* (2013.01); *B32B 27/065* (2013.01); *B32B 27/32* (2013.01); *E04F 15/02* (2013.01); *E04F 15/107* (2013.01); *E04F 15/187* (2013.01); *E04F 15/206* (2013.01); *E04B 9/045* (2013.01); *E04B 2001/8461* (2013.01); *E04F 2201/0107* (2013.01); *E04F 2201/0138* (2013.01); *E04F 2201/026* (2013.01); *E04F 2203/065* (2013.01)

(58) Field of Classification Search
CPC .............. E04B 9/045; E04B 2001/8461; E04F 2203/06; E04F 2203/065; E04F 2201/026; E04F 2201/0107; E04F 2201/0138; E04F 15/02; E04F 15/22; E04F 15/107; E04F 15/187; E04F 15/206; B32B 27/065; B32B 27/32
See application file for complete search history.

(56) References Cited

U.S. PATENT DOCUMENTS

| | | | | |
|---|---|---|---|---|
| 5,952,076 | A * | 9/1999 | Foster ..................... | B32B 27/32 428/215 |
| 2003/0219582 | A1* | 11/2003 | Ramesh .................. | E04F 15/18 428/304.4 |
| 2004/0123538 | A1* | 7/2004 | Ko .......................... | G09F 19/22 52/385 |
| 2006/0003148 | A1* | 1/2006 | Zwynenburg ............ | B32B 5/18 428/157 |

(Continued)

*Primary Examiner* — Jessie T Fonseca
(74) *Attorney, Agent, or Firm* — Francis C. Hand; Carella, Byane et al (57) ABSTRACT

The cushioning preform comprises two layers of foam material, e.g. polyethylene foam, laminated together in a laterally offset relation to one another, with or without a polyethylene film therebetween. Each of the foam layers is of rectangular cross-section has a surface section of greater density than the remaining section thereof. Rolls of the preform may be unrolled into a flattened condition on a substrate, such as a concrete floor, with a stepped edge of each unrolled preform overlaid by an adjacent unrolled preform and adhered thereto by a glue on the stepped edge.

23 Claims, 4 Drawing Sheets

(56) References Cited

U.S. PATENT DOCUMENTS

| | | | |
|---|---|---|---|
| 2008/0230309 A1* | 9/2008 | Fox | B32B 5/26 |
| | | | 181/286 |
| 2015/0075901 A1* | 3/2015 | Beresowski | E04B 1/86 |
| | | | 181/290 |
| 2015/0082730 A1* | 3/2015 | Atkinson | E04F 15/02177 |
| | | | 52/588.1 |
| 2016/0083965 A1* | 3/2016 | Baert | E04F 15/02188 |
| | | | 52/309.15 |
| 2016/0168864 A1* | 6/2016 | Ramachandra | E04F 15/107 |
| | | | 52/588.1 |
| 2018/0058077 A1* | 3/2018 | Alfieri | B32B 9/042 |

* cited by examiner

CUSHIONING PREFORM FOR FLOORING

This is a Non-Provisional Patent Application and claims the benefit of Provisional Patent Application 62/675,378, filed May 23, 2018.

This invention relates to a cushioning preform for flooring. More particularly, this invention relates to a floor having a cushioned foam incorporated therein.

As is known, various types of laminate foam flooring compositions have been proposed for use in combination with wood laminate flooring. For example, U.S. Pat. No. 5,952,076 describes a laminate composition of thin film of low density polyethylene adhered to a sheet of low density polyethylene foam by means of a very thin layer of low density polyethylene wherein one side of the polyethylene film extends beyond one edge of the polyethylene foam sheet. As described, the laminate composition is in long strips and is installed so that one edge of one strip overlies the extended portion of the polyethylene film of another strip. U.S. Pat. No. 6,607,803 describes a similar laminate composition but with a double sided tape is present on the top surface of the exposed edge of the film with a removable layer, such as of paper, that is removed after installation in order to receive another strip.

Briefly, the invention provides a cushioning preform for flooring made of a cushioned foam material of a size that can be laid on a sub-floor or other like surface and upon which a plurality of floor panels, for example, of wood, can be laid on top to provide a finished floor surface without the need for manipulating thin edges of film or removable paper layers In accordance with the invention, the cushioning preform comprises two layers of foam material, e.g. polyethylene foam, laminated together in a laterally offset relation to one another wherein each of the foam layers is of rectangular cross-section having a surface section of greater density than a remaining section thereof.

In one embodiment, a polyethylene film is laminated to and between the surface sections of the two foam layers. In this embodiment, the film extends across the bottom layer with a first exposed surface above the bottom layer and extends across the top layer with a second exposed surface below the top layer. Each of the exposed surfaces of the film is of a size to receive an application of a cohesive glue, i.e. a glue that adheres to itself but not other materials, such as a L3660 cohesive supplied by Baker Titon, of Patterson, N.J. The glue serves to adhere overlapping preforms to each other in side-by-side relation.

In another embodiment, the film extends across the top layer with an exposed surface below the top layer at one end of the bottom layer and the bottom layer projects beyond the top layer at an opposite end to form a lip without the film extending across the exposed lip of the bottom layer. Both the exposed surface below the top layer and the lip are of a size to receive an application of cohesive glue or a pressure sensitive glue or a strip of material with a cohesive glue thereon.

Where a separate strip of material with a cohesive glue thereon is used, the strip is made of a material that may be bonded to a foam layer under heat. For example, the strip of material is made of a plastic, such as polyethylene or poly propylene.

In another embodiment, two layers of foam material may be laminated directly to each other without the use of an intermediate polyethylene film between the two foam layers.

In use, rolls of the cushioning preform are unrolled onto a substrate, such as a concrete floor, one at a time with consecutively laid rolls overlapping each other in side-by-side relation.

The invention also provides a method of making a preform wherein two webs of foam are laminated in offset relation directly to each other under heat and pressure sufficient to bond the foam webs together while compressing a surface section of each web to a greater density than a remaining section thereof and while laminating the webs together into a laminated stream having an exposed lip along one side of the bottom layer and an exposed lip along one side of the top layer.

Thereafter, the resulting laminated stream is severed at predetermined intervals into a preform that is then rolled up for shipment and subsequent unrolling for installation purposes.

In another embodiment, a polyethylene film is positioned between the two webs of foam and laminated to and between the two webs of foam, In still another embodiment, the bottom layer of the preform may be embossed to allow air to be trapped when installed. In this embodiment, in order to visually distinguish the top layer from an embossed bottom layer of the preform, color may be added to one of the layers. For example, the top layer may be of a blue color to signify that the preform is to be installed with the blue surface "up".

These and other objects and advantages of the invention will become more apparent from the following detailed description taken in conjunction with the drawings wherein.

Figure 1:
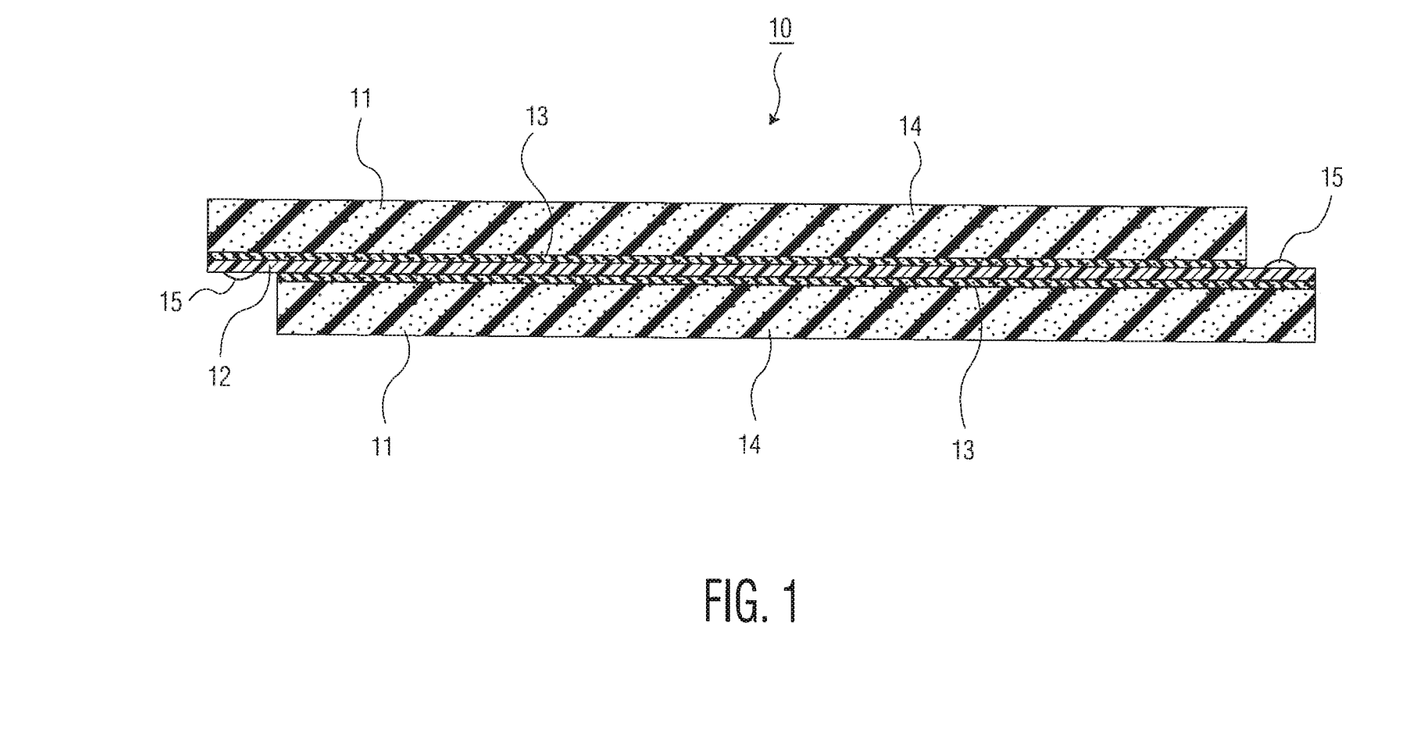
FIG. 1 illustrates a cross-sectional view of a preform in accordance with the invention.

Referring to FIG. 1, the cushioning preform 10 for flooring is comprised of two layers 11, 11' of foam material, e.g. polyethylene foam, laminated together by a polyethylene film 12 in a laterally offset relation to one another.

As illustrated, each layer of foam material 11, 11' is of rectangular cross-section having a surface section 13 of greater density than a remaining section 14 thereof. The polyethylene film 12 is laminated to and between the surface sections 13 of the two foam layers 11, 11' with an exposed edge surface on each lateral side of the preform 10. As illustrated, the film 12 extends across the bottom layer 11 with a first exposed surface above the bottom layer 11 and extends across said top layer 11' with a second exposed surface below the top layer 11'.

Figure 4:
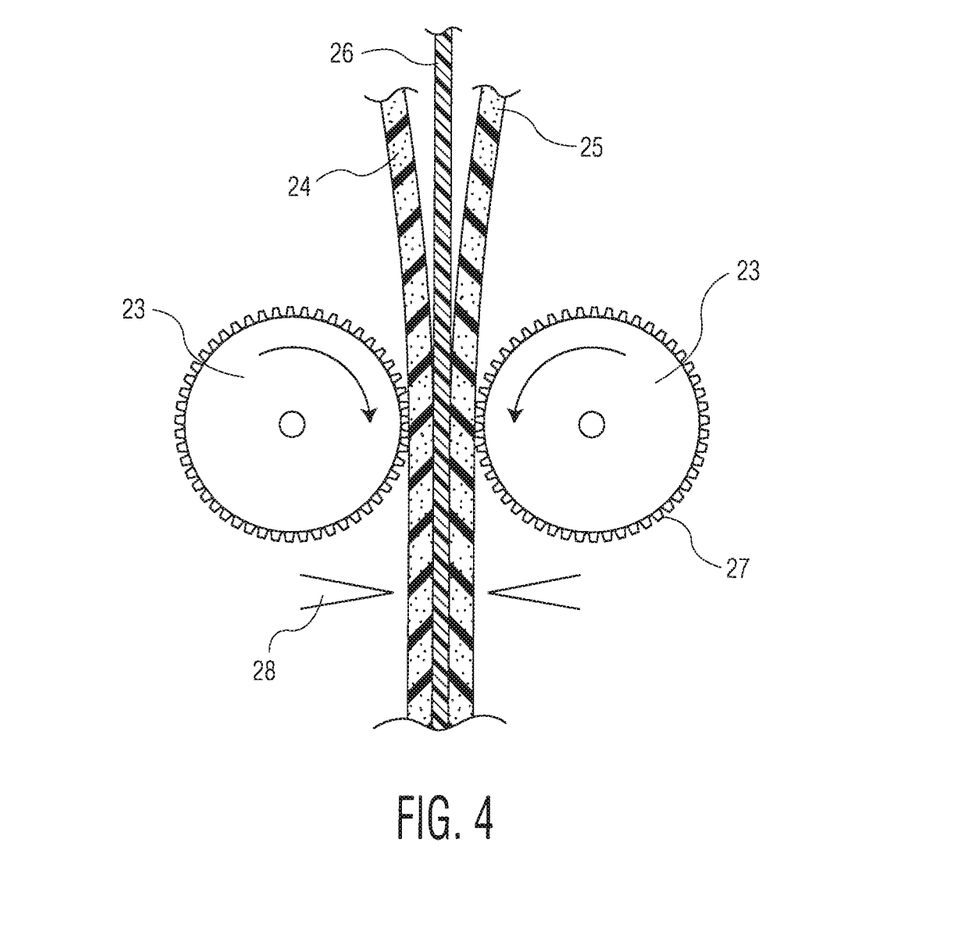
FIG. 4 schematically illustrates an apparatus for making the preform of FIG. 1.

Referring to FIG. 4, in accordance with the invention, a pair of rollers 23 is used to laminate two webs of foam 24, 25 with a heated web of polyethylene film 26 therebetween and in offset relation to each other under pressure sufficient to cause the heated polyethylene film 26 to bond the foam webs 24, 25 together.

The thickness of the foam webs 24, 25 may be of any suitable thickness for flooring with a preferred range of from 1/32 inch to % inch and the density of the foam in the range of 0.5 to 5.0 pounds per cubic foot (0.5 pcf).

The thickness of the polyethylene film is in the range of from 0.5 mil to 4.0 mil, and preferably 1.0 mil and the film is heated to a sufficient degree to become tacky in order to bond the two webs of polyethylene foam together while heating the surfaces of the two webs sufficiently to densify the surfaces of the two webs.

By way of example, laminating two webs of polyethylene foam having a thickness of 1/16 inch and a density of 1.2 pcf with a heated polyethylene film having a thickness of one mil and a density of 32 pcf under pressure results in a preform 10 with layers of foam material 11 each having a surface section 13 of a density that is greater than the density of the remaining section 14.

It is to be noted that the combination of heat and pressure causes only the surfaces of the two foam webs to densify without densifying the entire cross-section of the foams. For example, instead of the resulting preform having a thickness of 1/8 inch plus the thickness of the film, the preform has a thickness of 3/32 inch plus the thickness of the film. In this example, each foam web is reduced in thickness from 1/16 (4/64) inch to 3/64 inch.

By laminating in the above manner, the foam webs 24, 25 are caused to shrink thickness causing the two surfaces to densify. Due to the densifying of the surfaces, each surface presents a vapor barrier.

As indicated in FIG. 1, the resulting preform 10 thus has five (5) vapor barriers, each vapor barrier being provided by the two sections 13 of greater density, the two sections 14 of less density and the film 12. The nature of the materials of the preform 10 provide a vapor barrier, as is known, to water vapor, radon gas and the like.

In addition, the preform 10 is provided an application of a cohesive glue 15 on the two exposed edge surfaces of the film 12 for purposes of securing adjacently laid preforms 10 together in side-by-side relation. The glue 15 is characterized in being a glue that will only stick to itself, thereby eliminating the need for a release layer, such as paper, and facilitating installation, The preform 10 is provided in lengths that allow the preform 10 to be rolled up into rolls for shipment and use. For example, a roll of preform may have 10 feet or more of material. Laying of a floor can be performed in a relatively simple economical manner by simply rolling out one preform 10 and rolling a second preform 10 onto the side of the first preform 10.

The width of the preform 10 may be of any suitable width with a preferred range of from 24 inches to 96 inches.

Figure 2:
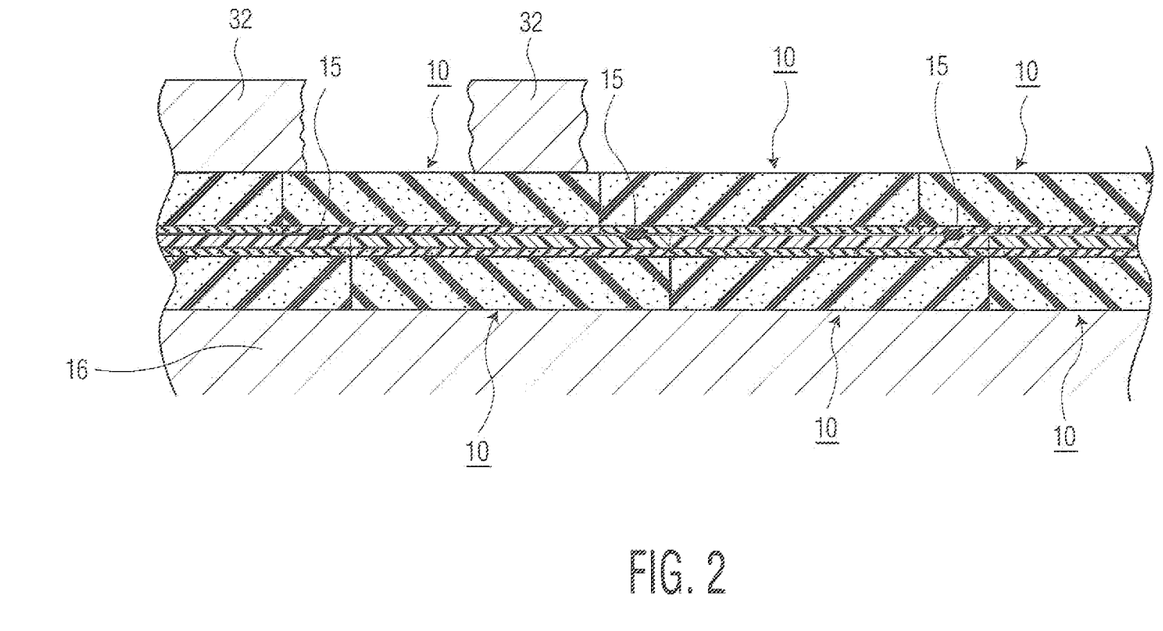
FIG. 2 illustrates a part cross-sectional view of a floor incorporating a plurality of preforms in accordance with the invention.

Referring to FIG. 2, in order to lay a floor, a plurality of cushioning preforms 10 are disposed in side-by-side relation.

As illustrated, after unrolling one preform 10 from a supply roll (not shown) into a flattened condition on a substrate 16, such as a concrete floor, the preform 10 shows a stepped edge on each side akin to FIG. 1. At this time, the glue 15 on the right-hand side, as viewed, is exposed.

Next, a second preform 10 is unrolled from a second supplied roll (not shown) so that the left-hand edge, as viewed, of the second preform 10 overlays the right-hand edge of the first preform 10 in mating side-by-side relation and is pressed down.

Thereafter, additional preforms 10 are unrolled and put into place in side-by-side relation.

After laying a floor, a plurality of floor panels 32, for example, of wood, can be laid on top to provide a finished floor surface.

The overlaps provided by the preforms 10 are smooth and uniform thereby providing a smooth and even surface for applying an overlying flooring of floor panels.

Figure 3:
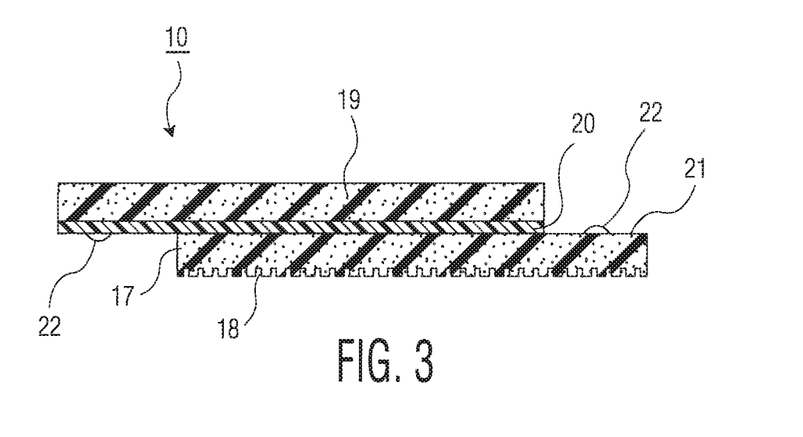
FIG. 3 illustrates a perspective view of a modified preform in accordance with the invention.

Referring to FIG. 3, in another embodiment, the cushioning preform 10' is fabricated with a bottom layer 17 of foam material having an embossed bottom surface 18; a top layer 19 of foam material laterally offset relative to the bottom layer 17; and a polyethylene film 20 laminated to and between the bottom layer 17 and the top layer 19.

As illustrated, the film 20 extends across the top layer 19 with an exposed surface below the top layer 19 at one end of the bottom layer 17 and the bottom layer 17 projects beyond the top layer 19 at an opposite end to form a flexible lip 21, In addition, an application of a cohesive glue 22 may be applied to the surface of the lip 21.

Referring to FIG. 4, an apparatus for making the preform of FIG. 1 includes a pair of rollers 23 for pressing the layers and film of the preform 10 together.

In accordance with the invention, one method of making the preform 10, requires the steps of:

generating a first web 24 of foam material;
generating a second web 25 of foam material;
generating a heated stream 26 of polyethylene film;
positioning the stream 26 of polyethylene film between the two webs 24, 25 with the two webs laterally offset relative to each other; and thereafter passing the two webs 24, 25 and film stream 26 between a pair of rollers 23 to press the webs 24, 25 and film stream 26 together with the film stream 26 at a temperature sufficient to laminate the film stream 26 to each of the webs 24, 25.

By way of example, in order to laminate two webs of polyethylene foam 24, 25 having a thickness of 1/16 inch with a polyethylene film 26 having a thickness of one mil, the rollers 23 should have a nip, i.e. distance apart, of 3/32 inch.

Of note, the stream 26 of polyethylene film may be heated by means (not shown) to a temperature sufficient to render the polyethylene tacky. As an alternative, the polyethylene may be extruded from an extruder in a molten form directly between the two webs 24, 25 of foam material at a point near to the nip formed by the two rollers 23.

The width of the webs 24, 25 may range from 24 to 96 inches.

This method produces a long length of material having a cross-section as illustrated in FIG. 1. This length may be severed transversely by a cutting device 28, for example, at intervals of 25 to 50 feet, and rolled up to form a bundle for shipment and subsequent unrolling for installation purposes. Multiple rolls of preform 10, each with stepped side edges, may then be unrolled and placed side-by-side on a substrate to making a flooring.

Alternatively, the produced length may be severed transversely at much smaller intervals, for example, at intervals of 12 to 24 inches, produce strips of preforms 10 with stepped sides that are adapted for end-to-end placement in making a flooring.

The preform 10 may also be of a length to form a square for laying on a sub-floor in the manner of conventional tiles.

One of the rollers 23 may have an embossing surface 27 for embossing one of the webs 24, 25 so that the bottom layer 11 has an embossed outer surface while the top layer 11' has a smooth surface. The embossed surface allows air to be trapped below the preform 10 within the embossments when installed on a substrate thereby adding to the cushioning characteristics of the preform 10 and providing a degree of sound deadening.

Alternatively, each of the rollers 23 may have an embossing surface for embossing the surfaces of each web 24, 25 so that the preform 10 has embossed top and bottom surfaces.

Providing the preform 10 with a bottom embossed surface allows any moisture that may be present between a substrate, such as a concrete floor, and overlying preforms 10 to be channeled to the sides of the preforms 10 by traffic walking across the laid floor panels. That is, the pressing down of footsteps causes air within the embossed surface to push any moisture to areas of lower pressure, typically along the perimeter of the preforms 10 that is not sealed.

In another embodiment, the two layers of foam material 23, 24 are glued together, for example, by a cohesive glue, for example, by directing a stream of glue between the foam webs 23, 24 being pressed together by the rollers 23 as indicated in FIG. 4. In this case, the webs 23, 24 do not have surfaces that are densified. Instead, the resulting layer of glue forms a vapor barrier.

Also, instead of using a cohesive glue 15 that will only stick to itself, a pressure sensitive glue may be used on the exposed edges of the preform 10 with overlying release strips.

Figure 5:
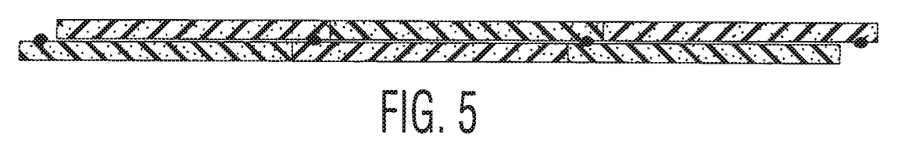
FIG. 5 illustrates a cross-sectional view of another embodiment of a preform in accordance with the invention.

Referring to FIG. 5, an embodiment of the cushioning preform 10" may be made without the polyethylene film or glue. In this embodiment, the preform 10" is formed of two webs of polyethylene foam 24, 25 that are laminated directly to each other thereby causing a higher density at the lamination point and resulting in three vapor barriers. The two webs 24, 25 are also laminated together in offset relation to each other to provide a lip 21 at the edge of each web 24, 25.

In addition, a cohesive glue 15 is applied to each lip 21 or a pressure sensitive glue may be used on the lips 21 with overlying release strips (not shown).

Figure 6:
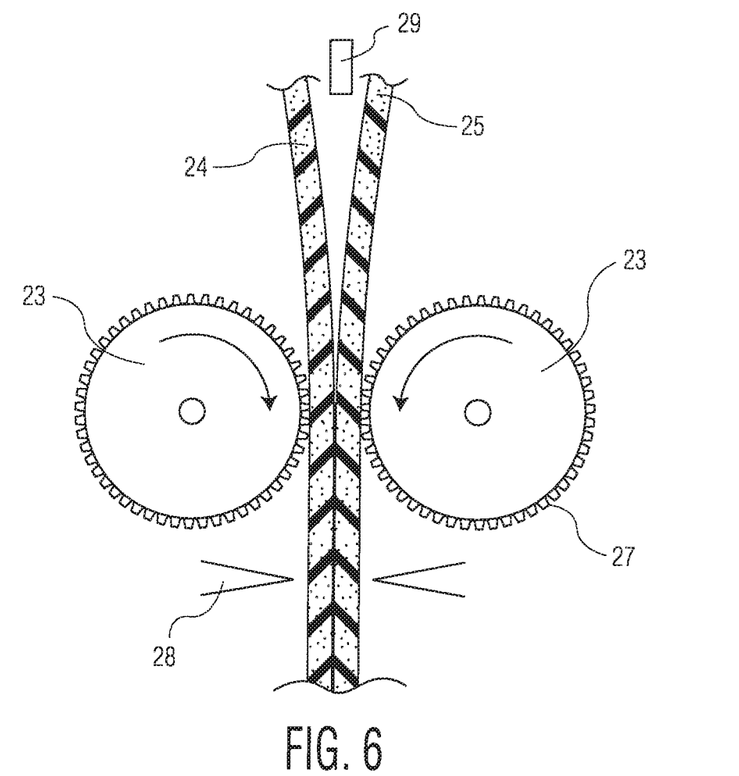
FIG. 6 schematically illustrates an apparatus for making the preform of FIG. 5.

Referring to FIG. 6, wherein like reference characters indicate like parts as above, the preform 10" is made using a pair of rollers 23 and a heating device 29. As illustrated, the heating device 29 is disposed above the rollers 23 and between the two webs of foam 24, 25 being delivered into the nip of the rollers 23. For example, the heating device 29 is an infrared heater of conventional construction suitable for the purpose of heating the two webs of foam 24, 25 prior to entry into the nip of the rollers 23.

The rollers 23 are spaced apart a distance sufficient to laminate the two heated webs of foam 24, 25 in offset relation to each other under a pressure sufficient to cause the two webs 24, 25 to bond directly to each other while densifying the heated surface sections 13 in direct contact with each other.

The thickness of the foam webs 24, 25 may be of any suitable thickness for flooring with a preferred range of from 1/32 inch to 1/2 inch and the density of the foam in the range of 0.5 to 5.0 pounds per cubic foot (0.5 pcf).

By way of example, laminating two webs of polyethylene foam having a thickness of 1/16 inch and a density of 1.2 pcf under heat and pressure results in a preform 10' with layers of foam material 11 having a surface section 13 of a density that is greater than the density of the remaining section 14.

It is to be noted that the combination of heat and pressure causes only the surfaces of the two foam webs 24, 25 to densify without densifying the entire cross-section of the foams. For example, instead of the resulting preform 10' having a thickness of 1/8 inch, the preform has a thickness of 3/32 inch. In this example, each foam web 24, 25 is reduced in thickness from 1/16 (4/64) inch to 3/64 inch, By way of example, in order to laminate two webs of polyethylene foam 24, 25 having a thickness of 1/16 inch, the rollers 23 should have a nip, i.e. distance apart, of 3/32 inch.

By laminating in the above manner, the foam webs 24, 25 are caused to shrink in thickness causing the two surfaces to densify. Due to the densifying of the surfaces, each surface presents a vapor barrier.

Of note, laminating the foam webs 24, 25 directly to each other causes the two sections 13 of greater density to fuse into one vapor layer. Thus, as indicated in FIG. 5, the resulting preform 10' has three (3) vapor barriers, each vapor barrier being provided by the two fused sections 13 of greater density and the two sections 14 of less density. The nature of the materials of the preform 10" provide a vapor barrier, as is known, to water vapor, radon gas and the like.

A preform may also be made wherein each of the pair of rollers 23 is heated along with the heating device 29 disposed above the rollers 23 and between the two webs of foam 24, 25 being delivered into the nip of the rollers 23, In this embodiment, the facing surfaces of the two webs of foam 24, 25 are heated by the heating device 29 before entering the nip of the rollers 23 causing the two surfaces to shrink in thickness and to densify. In addition, the outer surfaces of the two webs of foam 24, 25 are heated by the rollers 23 in the nip of the rollers 23 causing the two surfaces to shrink in thickness and to densify.

The resulting preform would have five (5) vapor barriers, each vapor barrier being provided by the fused sections of greater density between the foam webs 24, 25, the two sections of greater density on the outer surfaces of the foam webs and the two sections of less density within the foam webs 24, 25.

Figure 7:
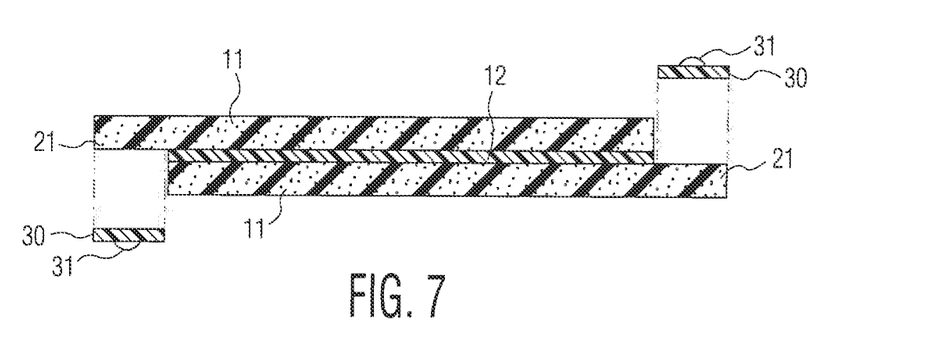
FIG. 7 illustrates a partially exploded cross-sectional view of another embodiment of a preform in accordance with the invention.

Referring to FIG. 7, wherein like reference characters indicate like parts as above, a polyethylene film 12 may laminated to and only between the facing surfaces of the two foam layers 11, 11' without an exposed edge surface of the film on each lateral side of the preform 10.

As illustrated, the cushioning preform 10" is comprised of two layers 11, 11' of foam material, e.g. polyethylene foam, laminated together by a polyethylene film 12 in a laterally offset relation to one another without the film 12 extending beyond the edges of the foam layers 11, 11' so as to define an exposed lip 21 along one side of the bottom layer 11 and an exposed lip 21 along one side of the of the top layer 11'.

In this embodiment, a first strip of material 30 is disposed on the exposed lip 21 of the bottom layer 11 along with a cohesive glue 31 thereon; and a second strip of the same material 30 is disposed on the exposed lip 21 of the top layer with a cohesive glue 31 thereon. The strips of material 30 may be applied during manufacture of the cushioning preform 10". Typically, the strips of material 30 are made of a plastic such as polyethylene or polypropylene.

The roam material may also be made of polypropylene or any other suitable foam material, such as a polystyrene. For the same density, the use of a polyethylene foam imparts a spongy sound deadening characteristic to the preform and the use of a polystyrene foam imparts a more rigid characteristic to the preform and allows the preform to be more easily put down in use.

The preform of the invention allows a floor to be constructed in a relatively simple, efficient manner in a minimum of time since there are no release layers or tapes that need to be removed before the preform is ready to unroll onto a sub-floor.

The invention thus provides a cushioning preform that may be made in an economical manner.

What is claimed is:

1. A cushioning preform for flooring comprising
a bottom layer of foam material of rectangular cross-section having a top surface section of greater density than a remaining section thereof; and
a top layer of foam material of rectangular cross-section having a bottom surface section of greater density than a remaining section thereof, said top layer being laterally offset relative to said bottom layer and laminated to said bottom layer to define an exposed lip along one side of said bottom layer and an exposed lip along one side of said of said top layer.

2. A cushioning preform as set forth in claim 1 further comprising a polyethylene film laminated to and between said top surface section of said bottom layer and said bottom surface section of said top layer.

3. A cushioning preform as set forth in claim 2 wherein said film has a first exposed surface above said lip of said bottom layer and a second exposed surface below said lip of said top layer.

4. A cushioning preform as set forth in claim 3 further comprising a first application of cohesive glue on said first exposed surface of said film; and a second application of cohesive glue on said second exposed surface of said film.

5. A cushioning preform as set forth in claim 3 further comprising a first strip of material on said exposed lip of said bottom layer with a cohesive glue thereon; and a second strip of material on said exposed lip of said top layer with a cohesive glue thereon.

6. A cushioning preform as set forth in claim 2 wherein said bottom layer has a thickness of 3/64 inch, and said film has a thickness of 1 mil.

7. A cushioning preform as set forth in claim 1 wherein said foam material of each said bottom layer and said top layer is a polyethylene foam.

8. A cushioning preform as set forth in claim 1 further comprising a first application of cohesive glue on said lip of said bottom layer and a second application of cohesive, glue on said lip of said top layer.

9. A cushioning preform as set forth in claim 1 wherein said bottom layer of foam material has an embossed bottom surface.

10. A cushioning preform as set forth in claim 7 wherein said top layer of foam material has an embossed top surface.

11. A cushioning preform comprising
a bottom layer of foam material of rectangular cross-section having a top surface section of greater density than a remaining lower section thereof to form a vapor barrier;
a top layer of foam material of rectangular cross-section having a bottom surface section of greater density than a remaining lower section thereof to form a vapor barrier, said top layer being laterally offset relative to said bottom layer to define an exposed lip along one side of said bottom layer and an exposed lip along one said of said top layer; and
a polyethylene film laminated to and between said bottom layer and said top layer to form a vapor barrier.

12. A cushioning preform as set forth in claim 11 wherein said film extends across said bottom layer with a first exposed surface above said lip of said bottom layer and extends across said top layer with a second exposed surface below said lip of said top layer.

13. A cushioning preform as set forth in claim 12 further comprising a first application of cohesive glue on said first exposed surface of said film; and a second application of cohesive glue on said second exposed surface of said film.

14. A flooring comprising
a plurality of cushioning preforms disposed in side-by-side relation, each said preform being made of a bottom layer of foam material of rectangular cross-section having a top surface section of greater density than a remaining section thereof; and a top layer of foam material of rectangular cross-section having a bottom surface section of greater density than a remaining section thereof, said, top layer being laterally offset relative to said bottom layer to define an exposed lip along one side of said bottom layer and an exposed lip along one said of said top layer.

15. A flooring as set forth in claim 14 further comprising a polyethylene film laminated to and between said top surface section of said bottom layer and said bottom surface section of said top layer, said film having a first exposed surface above said lip of said bottom layer and a second exposed surface below said lip of said top layer.

16. A flooring as set forth in claim 15 further comprising an application of cold seal glue between said first exposed surface of said film of one of said preforms and said second exposed surface of said film of another adjacent one of said preforms to secure said one and said other preforms together.

17. A flooring as set forth in claim 16 further comprising a plurality of floor panels disposed on said plurality of cushioning preforms.

18. A floor as set forth in claim 17 wherein said floor panels are made of wood.

19. A method of making a preform comprising the steps of
generating a first web of foam material;
generating a second web of foam material;
positioning said first web and said second web in facing relation with said first web laterally offset relative to said second web;
heating facing surfaces of each of said first web and said second web; and
passing said first web and said second web between a pair of rollers to press said first web and said second web together while compressing said facing surfaces of each of said first web and said second web to a greater density than a remaining section thereof and while laminating said first web and said second web together into a laminated stream having an exposed lip along one side of said bottom layer and an exposed lip along one side of said top layer.

20. A method of making a preform as set forth in claim 19 further comprising the steps of
generating a stream of heated polyethylene film,
positioning said stream of polyethylene film between said first web and said second web to heat said facing surfaces of each of said first web and said second web, and
passing said first web, said polyethylene film and said second web between said pair of rollers to press said first web, said polyethylene film and said second web together into said laminated stream.

21. A method of making a preform as set forth in claim 19 wherein said rollers are heated to heat the outer surfaces of each of said first web and said second web to a greater density than a remaining section thereof.

22. A method as set forth in claim 20 further comprising the step of severing the laminated stream transversely at predetermined intervals of length to form a preform for rolling up for shipment.

23. A method as set forth in claim 19 wherein at least one of said rollers has an embossing surface for embossing at least one of said webs.

\* \* \* \* \*

UNITED STATES PATENT AND TRADEMARK OFFICE
CERTIFICATE OF CORRECTION

| | |
|---|---|
| PATENT NO. | : 11,280,096 B1 |
| APPLICATION NO. | : 16/409050 |
| DATED | : March 22, 2022 |
| INVENTOR(S) | : Harry Bussey et al. |

It is certified that error appears in the above-identified patent and that said Letters Patent is hereby corrected as shown below:

In the Specification

Column 3, Line 3, "0/0" should be --1/2--

Column 6, Line 56, "roam" should be --foam--

Signed and Sealed this
Tenth Day of May, 2022

Katherine Kelly Vidal
*Director of the United States Patent and Trademark Office*